United States Patent [19]

Sipin

[11] Patent Number: 5,000,052
[45] Date of Patent: Mar. 19, 1991

[54] CONTROLLED SAMPLER

[76] Inventor: Anatole J. Sipin, 221 E. 78th Street, New York, N.Y. 10021

[21] Appl. No.: 353,249

[22] Filed: May 17, 1989

[51] Int. Cl.$^5$ .............................................. G01N 1/24
[52] U.S. Cl. .................................................. 73/863.03
[58] Field of Search ........... 73/863.03, 864.34, 863.83, 73/28; 417/43, 63

[56] References Cited

U.S. PATENT DOCUMENTS

| | | | |
|---|---|---|---|
| 3,784,902 | 1/1974 | Huber | 73/863.03 X |
| 3,965,748 | 6/1976 | Boubel et al. | 73/863.03 |
| 4,067,705 | 1/1978 | Kurz | 73/863.03 |
| 4,237,451 | 12/1980 | Hollenbeck | 73/28 X |
| 4,432,248 | 2/1984 | Lalin | 73/863.03 |
| 4,566,342 | 1/1986 | Kurz | 73/863.03 |
| 4,569,235 | 2/1986 | Conkle et al. | 73/863.03 |

Primary Examiner—Hezron E. Williams
Assistant Examiner—Joseph W. Roskos
Attorney, Agent, or Firm—Hedman, Gibson, Costigan & Hoare

[57] ABSTRACT

The present invention is concerned with a controlled sampler device which draws a gas through a contaminant collection device. The controlled sampler comprises an inlet to the sampler; a pump adapted to draw a gas through the inlet; a reference element that provides a reference signal; a feedback element with an output; a differential pressure transducer to compare the reference signal with the feedback signal to provide an error signal that is linearly related to selected and measured values; an integrator with an input connected to the output of the differential pressure transducer and to a summer; and means between the differential pressure transducer and the summer to provide a signal to the summer which is proportional to the error signal, which is passed to a driver which regulates the speed of an electric motor to change the flow rate to reduce the error signal to a null.

22 Claims, 9 Drawing Sheets

CONTROLLED SAMPLER

BACKGROUND OF THE INVENTION

This invention relates to the sampling of environmental air for the purpose of measuring levels of airborne contaminants for protection against pollutant related diseases. For a number of years personal and area sampler pumps have been used to draw air samples of known volumes through collection devices, such as filters, to collect particulates in the sampled air volume, and sorbent tubes to trap vapors and gases for future analysis, as well as direct reading colorimetric indicator tubes. Pumps have also been used for direct collection of air samples for analysis. Although fixed volume grab samples are sometimes taken, these are usually for reasons of immediate safety, and for long term health protection, the air sampled should be taken at a constant rate over an extended period of time to provide a time-weighted average measure of the contaminant concentration. Personal sampler pumps are designed to be worn by the individual being monitored for a number of hours, so as to obtain a measure of the average concentration of contaminant breathed by an ambulatory worker or other individual at various locations. Area sampler pumps are usually larger and stationary, and they are designed to sample much larger volumes of air at higher flow rates, to determine average contaminant concentration over time at a particular location.

The health hazard caused by airborne asbestos fibers has become widely recognized in the past decade. Various governmental regulations on the federal, state and local levels have been promulgated for the removal of asbestos from existing structures and vehicles. Asbestos had been so widely used for insulation and fire protection that complete removal from schools and other public and private buildings, as well as ships, will require several more years. Immediate application of the subject invention is for area monitoring at sites of asbestos removal, both to determine the existing hazard posed by prior levels of airborne asbestos, as well as to assure the safety of an area after completion of asbestos removal. The application is not limited to asbestos monitoring, however, as there are continuing hazards from other airborne dusts such as silica, cotton dust, etc., which provide requirements for an improved sampler. The invention also has application as an improved personal sampler, both for particulates and gas monitoring.

There are certain limitations of sampler pumps currently available. Existing portable pumps do not use direct measurement of the true volumetric flow rate to set and control the flow rate of sampled air, but these are usually inferred. The flow rate is frequently set by connecting the pump to an external meter at the beginning of the sampling period, and an inferential control is used to maintain constant flow. Also, where a flow indicator is supplied with the pump, it is usually of poor accuracy, such as a small rotameter, and it is located on the outlet of the pump where an erroneous indication can occur due to leakage in the pump and pneumatic line. This is illustrated by current regulations for asbestos sampling, in which the outlet flow rate must be measured with the inlet blocked to test for leaks. There is, at present, no device that uses selection and direct measure for control of the flow of primary interest between the collection device and the pump in units of air volume at ambient conditions. Since the pressure and temperature in the line between the collection device and pump can vary, it is necessary to correct the direct measurement of this flow rate to provide the actual atmospheric volume being sampled, upon which standards are based.

Baker and Clark in U.S. Pat. No. 4,063,824 show a control in which the pressure drop across a constant orifice (or valve) is maintained at a constant value by means of a pressure switch and integrator, which vary the pump speed. To change the flow rate, however, an external flowmeter must be connected, and the valve setting changed, a procedure which is difficult to accomplish satisfactorily in the field.

Lalin in U.S. Pat. No. 4,432,248, and Hollenbeck in U.S. Pat. No. 4,237,451 describe control systems in which the flow rate is manually set prior to sampling, and the flow rate is controlled by adjusting pump speed in relation to increase in motor current caused by loading of a (particulate) collection filter.

Some area sampling pumps are driven through line cords by AC motors, whose speeds cannot be readily changed. In an attempt to maintain constant flow rate during a test, a critical orifice is sometimes placed between the collection filter and the pump. The large pressure drop across the orifice to maintain critical flow is wasteful of energy, and variations in the high pressure drops across the collection filter associated, for example, with asbestos sampling, can introduce considerable error.

At asbestos removal sites, area samplers that use AC motors are frequently stopped or interrupted by power failures or disconnection of the line cord, which can stop or destroy the validity of a test.

Total sampled air volume is a primary measured quantity, which must be known to calculate concentration. Present pumps use timers which infer the volume from an assumed constant flow rate. Even when electronic timers are included as part of the pump control, the reading can be lost due to power interruption.

There is a need for a controlled sampler in which a true volumetric flow rate can be variably selected as part of the control system, and in which the true volumetric flow rate through the collection device is directly measured and controlled.

Ther is also a need for a controlled sampler in which the total volume is measured and retained in a memory, even in the event of power failure, until physically reset.

There is a further need for a controlled area sampler that can be powered from an AC line or battery, and in which an auxiliary battery can be connected so that a smooth transfer from the line to the battery occurs in the event of a power failure, preserving the continuity of a test.

It is the purpose of the present invention to meet these needs, as well as other objectives.

SUMMARY OF INVENTION

The invention is basically a controlled sampler to draw a sample of air loaded with a contaminant, such as asbestos, through a contaminant collection device, such as a filter, at a constant selected volume flow rate, referred to ambient conditions prevailing in the atmosphere from which the air sample is drawn.

The controlled sampler includes
a DC motor-driven air pump,
a reference element to provide a reference signal that is linearly related to the selected value of sampled volume flow rate at the ambient conditions,
a flow sensor situated in the line between the collection device and the air pump, to provide a feedback signal, linearly related to the actual volume flow rate at ambient conditions passing through the collection device,
a differential amplifier to provide a flow rate error signal proportional to the difference between the reference and feedback signals,
an integrating amplifier and a proportional amplifier, connected in parallel, each responsive to the error signal from the differential amplifier, and each providing an output to a summer, which provides a signal proportional to the error signal and to its integral to a driver, which modulates the power to the pump motor so as to change the speed of the pump and the flow rate in a direction to reduce the error to a null.

Another feature of the invention is the use of a differential pressure laminar flow sensor and a pressure sensor to measure the negative pressure at the inlet to the laminar flow sensor, whose outputs are combined in a circuit which modifies the volumetric flow rate output of the flow sensor at conditions in the line to provide a measure of volumetric flow rate referred to ambient conditions.

An additional feature of the invention is the use of a laminar flow sensor with spaced apart taps consisting of a stack of parallel flow channels each having a rectangular flow path with a large aspect ratio of width to height, and constructed of solvent-welded acrylic plastic to provide repeatable performance with economical fabrication.

Yet another feature is the use of the basic control system to control another flow-related parameter, such as inlet pressure, at a selected constant value by adjustment of pump speed.

DETAILED DESCRIPTION OF THE INVENTION

Figure 1:
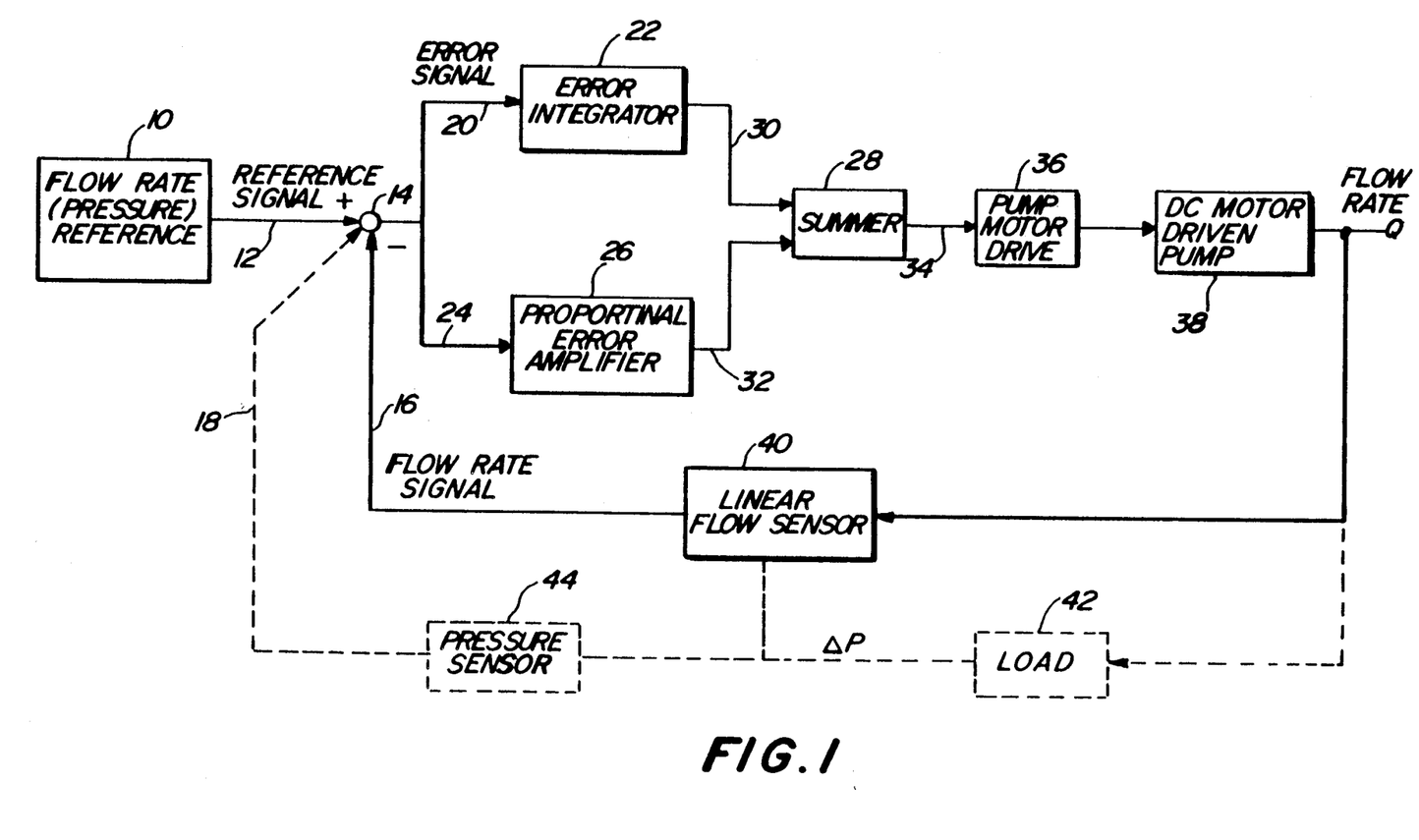
FIG. 1 is a functional block diagram of the controlled sampler system.

Referring to FIG. 1 it is seen that a reference element 10 provides a reference signal for a controlled flow-related parameter, which, for example, could be flow-rate or pressure, on reference lead 12. This is differentially compared at point 14 with a feedback signal for the flow-related parameter as, for example, a measured flow rate feedback signal on feedback lead 16, or a measured pressure feedback signal on feedback lead 18. The differential output signal is linearly related to the error between the selected and measured values of the parameter being maintained, for example, flow-rate or pressure, which is fed on line 20 to an integrator 22 and on line 24 to a proportional means 26, such as an amplifier with a constant gain. The output of the integrator is a signal related to the integral of the error signal, and it is fed to a summer 28 through lead 30. The output of the proportional means is a signal proportional to the error signal, and it is fed to summer 28 through lead 32. The summer provides an output driving signal, constituting the sum of the input integral and proportional signals, on lead 34 to a pump motor drive 36, which modulates electric power applied to the motor of a DC motor-driven pump 38, which pumps air or gas through a linear flow sensor 40, at a flow rate that varies as the speed of the pump. The output of the flow rate sensor 40 is identical wth the flow rate feedback signal on lead 16. If a load 42, such as a contaminant collection device, is connected to the pump, the flow rate passing through the load produces a pressure drop, which can be sensed by a pressure sensor 44, which provides an output identical with the pressure feedback signal on lead 18. The load 42 is not a part of the basic system for a controlled sampler package, but it becomes an operative part of the system when it is connected to the pump. In operation, when an error signal appears on leads 20 and 24, the proportional amplifier 26 will rapidly provide a signal proportional to the error through lead 32, whereas the output of the integrator on lead 30 will begin at zero and only gradually increase. The initial driving signal on lead 34, therefore, will cause the motor drive power to be varied so as to change the pump speed in a direction to reduce the error. Since the pump speed varies directly with the error, the error cannot be reduced to zero, and the minimum residual value of error depends on the gain of the proportional amplifier. As the integrated error signal on line 30 builds up, the error decreases and the proportional signal on line 32 decreases. This process will continue until the integrated signal on line 30 is sufficiently high to drive the error to zero, at which time the proportional error signal on line 32 will become zero. Thus, the control achieves a fast correction with a finite error and a slow adjustment that causes the error to disappear after a longer period.

Figure 2:
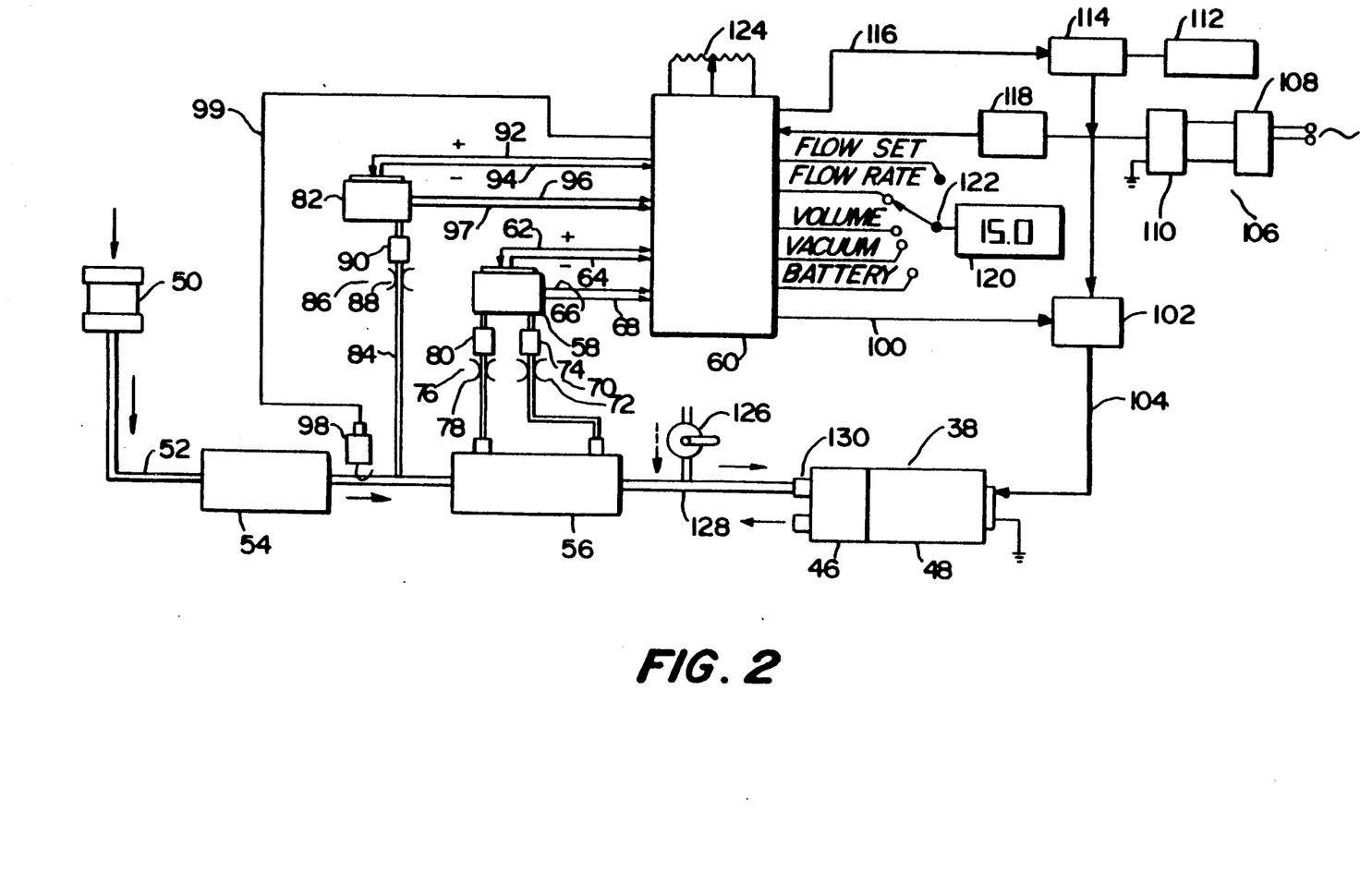
FIG. 2 is a schematic diagram of the system, more clearly showing relationships among the major elements.

FIG. 2 is a schematic diagram that illustrates a preferred mode of operation of the controlled sampler system. In this mode pump 38 consists of vacuum pump 46 driven by DC motor 48. The vacuum pump draws contaminated air from the atmosphere through a contaminant collection device such as particle collection filter 50. Air is drawn through filter 50, line 52, pulsation damper 54 and through a laminar flow rate sensor 56 into the inlet of vacuum pump 46. Because of the high pressure drops that can occur across the particle collection filter, vacuum pumps for such applications are usually, but not necessarily, positive displacement types, either vane, piston or diaphragm pumps. All such pumps cause some degree of pulsation in the flow, and it is frequently desirable to minimize such pulsations through use of a pulsation damper. The damper can be an accumulator type with a flexible membrane, or simply an enclosed volume which acts as a pneumatic capacitance.

The linear flow sensor specified in FIG. 1 is advantageous for feedback control systems due to a constant gain. Although dynamic types of sensors with a square law relationship between flow and pressure drop can be used, the control range is limited because of the severe gain change, and the measurement range is also less than that for a linear flow sensor. The linear flow sensor could be of a thermal type, many of which provide outputs proportional to mass flow rate, or of a laminar flow differential pressure type, in which the pressure drop across the sensor is directly proportional to the velocity and the viscosity of the fluid. The laminar flow sensor is preferable to a thermal type because the response can be much faster, which is advantageous for high accuracy and stable control. Since such sensors can use pressure transducers that require very little power, they also have an advantage for portable applications over thermal sensors which require a significant amount of power. As shown in FIG. 2, laminar flow sensor 56 has spaced apart pressure taps in the direction of flow which are connected to a differential pressure transducer 58. Pressure transducer 58 can be of the strain gage type, but it can also be of other types such as capacitive, inductive, etc. Control unit 60 supplies positive and negative excitation voltages to transducer 58 through lines 62 and 64. Transducer 58 includes a resistive strain gage bridge, and the outputs of the bridge, proportional to differential pressure, are fed to control unit 60 through lines 66 and 68. Although pump pulsations are attenuated by pulsation damper 54, the pneumatic ripple can still be high enough to adversely affect control stability. For this reason it has been found necessary to apply pneumatic pulsation attenuation in the pressure lines between the laminar flow sensor 56 and transducer 58. Pneumatic filter 70 which comprises restriction 72 and volume 74 is placed in the line between the downstream pressure tap of laminar flow sensor 56 and the low pressure port of differential pressure transducer 58, and pneumatic filter 76 which comprises restrictor 78 and volume 80 is placed in the line between the upstream pressure tap of sensor 56 and the high pressure port of transducer 58. The inlet pressure through laminar flow sensor 56 is sensed by gauge pressure transducer 82, which, as shown in FIG. 2, is of the same type as differential pressure transducer 58. Since the gauge pressure between the particle collection filter and the vacuum pump is negative, line 84 feeding pressure to transducer 82 is connected to the low pressure port. As for the case with transducer 58, it has been found that a pneumatic filter in line 84 to transducer 82 is advantageous. Filter 86 in line 84 consists of restrictor 88 and volume 90. Transducer 82 is excited by positive and negative voltages through lines 92 and 94, and the output of the strain gage bridge of transducer 82 is fed to control unit 60 through lines 96 and 97. An air temperature sensor 98 is placed in the air inlet line to the laminar flow sensor 56, and the temperature output is fed to control unit 60 through lead 99 to compensate for the effects on air viscosity and density of temperature variations.

A motor drive signal is supplied by control unit 60 through lead 100 to motor power control 102, which supplies current to the motor through line 104. Current can be supplied to the motor power control 102 from DC power supply 106, including a step-down transformer 108, which is energized from an AC line, and rectifier unit 110. DC power can also be supplied from optional DC battery 112 through a battery connecting relay 114. While power is being provided from supply 106, relay 114 is energized in the open position by a signal on lead 116 from the control unit 60. If supply 106 fails or AC power is disconnected, relay 114 will be de-energized in its normally closed position and it will connect battery 112 to provide the system power. DC power is fed from supply 106 or battery 112 to control power supply 118 which supplies DC power at high and low, positive and negative voltage levels to control unit 60. Control unit 60 supplies flow set, flow rate, volume, vacuum and battery condition signals to visual indicator 120 through selector switch 122. A flow rate or vacuum reference, depending on the mode of operation, is selected by positioning potentiometer 124.

When lower flow rates are selected for control, it is necessary for the pump to operate at a relatively slow speed, and all the flow through the pump is drawn through collector 50 and flow sensor 56. With some pumps, particularly diaphragm pumps, pulsation frequency at these slow speeds is very low and it becomes difficult to filter out the low frequencies, with resultant control instability. To overcome this problem and to increase the flow range, bypass valve 126 is provided between atmosphere and line 128, which connect flow sensor 56 to inlet 130 of the vacuum pump. When bypass valve 126 is open, the pump must draw considerably more air to achieve the desired low flow rate through collector 50, and, therefore, it will run at higher speeds, with higher pulsation frequencies, which do not affect control and stability. Since the flow sensor 56 is directly connected to the collector 50, and directly measures the sampled air, bypassed air into the pump inlet does not affect the accuracy of measurement or control. It should be noted that this arrangement also makes the system insensitive to pump leakage, which is a well recognized problem for many sampler pumps.

Figure 3:
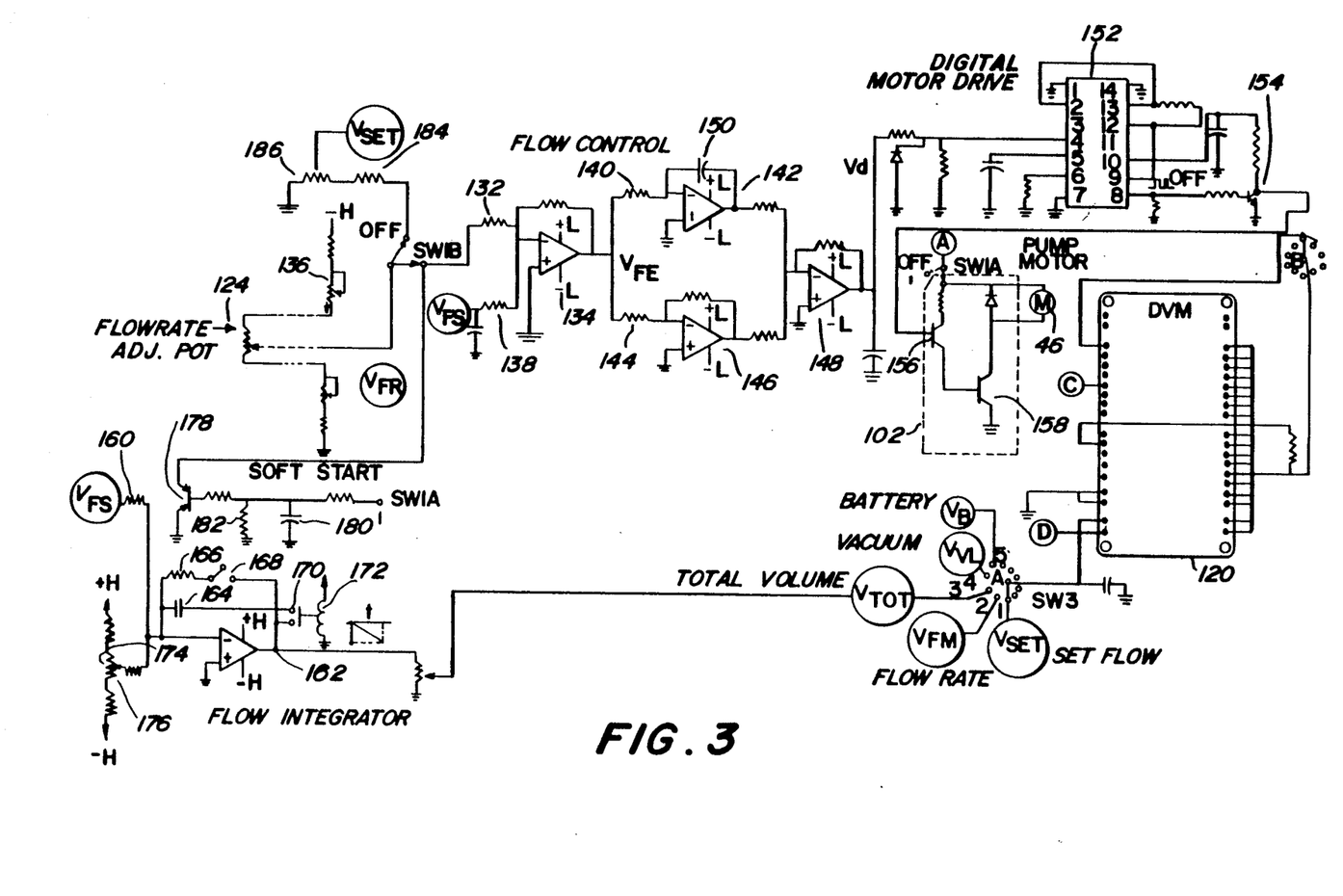
FIG. 3 is an electrical schematic diagram for a flow control system.

Operation of the control system can be understood in greater detail by referral to the electrical schematic diagram of FIG. 3, in which the controlled flow-related parameter is shown to be the volumetric flow rate. A flow rate reference voltage, $V_{FR}$, is fed from the wiper arm of potentiometer 124 through pole B of On-Off switch SW1, shown in the "On" position, through resistor 132 to the negative summing terminal of operational amplifier 134. The potentiometer is connected in a series voltage divider 136, which is energized from a negative high regulated voltage source in power supply 118, so that the reference voltage, $V_{FR}$, is of negative polarity. Feedback voltage, $V_{FS}$, from the linear flow sensor also is fed through resistor 138, which has the same value as resistor 132, to the summing terminal of amplifier 134. The feedback voltage is of positive polarity, so that the output voltage, $V_{Fe}$ of operational amplifier 134 is proportional to the difference between the reference and feedback voltages, and, therefore, to the flow rate error.

The flow rate error voltage is fed to the input resistor 140 of integrating amplifier 142, and it is fed, also, to the input resistor 144 of proportional amplifier 146. The outputs of integrating amplifier 142 and proportional amplifier 146 are of the same polarity, and they are added by summing amplifier 148, whose output voltage, $V_d$, is proportional to the sum of the error, as well as its time integral. That is, $V_d = K_1 V_{Fe} + K_2/R_1 C_B \int_0^t V_{Fe} dt$, where $R_1$ is the resistance of input resistor 140, $C_B$ is the capacitance of feedback capacitor 150 of integrating amplifier 142, $K_1$ and $K_2$ are constants, and t is time. Voltage $V_d$ is supplied to the input of a pulse-width modulator 152, whose output is a train of pulses at a relatively high frequency on the order of 10 KHz to 40 KHz, and in which the pulse duration varies directly with the amplitude of the input drive voltage $V_d$. The output pulse train of modulator 152 is fed to the base of switching transistor 154, which, in turn, actuates switching drive transistor 156, which is in a Darlington connection with switching power transistor 158. Power transistor 158 switches high current through pump motor 46 from a non-regulated DC power source in power supply 118 through pole A of on-off switch SW1, for an average duration determined by the duty cycle of the applied pulses.

If a step change in the reference or the flow rate is experienced, it is evident that the error correcting voltage $V_d$ will change by an amount proportional to $K_1$ at time $t=0$. Although there will be a rapid reduction in the error, the characteristic of proportionality requires a finite error, which will be inversely related to the loop gain. Voltage $V_d$ will continue increasing, however, due to the integral term, until the error voltage, $V_{Fe}$, and, therefore, the flow rate error, become effectively zero. Although a high loop gain will minimize proportional error, it will induce instability due to lags in the closed loop, including that due to motor-pump inertia, and those due to electrical and pneumatic filters, which are required to attenuate flow pulsations. It has been discovered that for a type of pump adequate for asbestos sampling, for example, at a flow rate of 15 liters/min at a characteristic inlet vacuum of 5 psi or over, an error of less than 3 to 5% cannot be achieved with a stable proportional control. With the addition of a parallel integral control, however, such an error is temporarily acceptable, as it will disappear after a period depending on the time constant $R_1 C_B$, of the integrator. If the error is integrated out in too short a period, there will be interaction with other system lags, and the control will again become unstable. Such a control will function best with moderate system gain and a moderately long integration time. It has been found that an initial summing amplifier 134 with a moderate gain on the order of 5 to 1 is required for effective performance of the parallel integrating amplifier 142 and proportional amplifier 146.

The outut voltage, $V_{FS}$, from the linear flow sensor, that is proportional to volumetric flow rate, is also fed through an input resistor 160, to an integrating amplifier 162, that has a feedback capacitor 164. The output of the flow rate integrator is a voltage $V_{TOT}$ that is proportional to the total volume that has been pumped during a sampling period. At the end of a the sampling period, the integrator is reset by discharging capacitor 164 through a resistor 166 by a momentary switch 168, which returns the output voltage $V_{TOT}$ to zero. Capacitor 164 is connected to the circuit throuth the normally open contacts 170 of a relay 172, which is energized from the power supply. In the event of a power disruption, relay 172 is de-energized, opening contacts 170 and maintaining the charge on capacitor 164. Thus, the total sampled volume information is retained even though power is removed, so that the sampled volume can be determined at a later time when power has been restored. To begin a new sampling period the capacitor is discharged through switch 168. Drift in amplifier 162 that could cause a erroneous output is periodically compensated by a zeroing signal from potentiometer 174 through resistor 176.

Rotary selector switch SW3 applies any of five voltages, representing five quantities, to digital indicator 120 through pole A. The quantities and corresponding voltages are flow rate setting, $V_{SET}$; measured flow rate, $V_{FM}$; total volume, $V_{TOT}$; inlet vacuum, $V_{VL}$, and battery charge, $V_B$. Pole B of switch SW3 connects appropriate terminals on indicator 120 to properly set the decimal point for the digital quantity displayed.

When the sampler is initially started through on-off switch SW1, there is a large error and a maximum value of $V_d$, which drives the pump to its maximum speed. It may require 10 to 20 seconds or longer for the system to stabilize, which is disconcerting to the operator. To eliminate this phenomenon a soft start circuit has been introduced. When the motor-driven pump is off, pole A of switch SW1 connects high voltage to terminal 1, which turns on PNP transistor 178, and effectively grounds the (reference) input to resistor 132 of differential amplifier 139, making the error voltage, $V_d$, zero. During this condition, capacitor 180 is charged to the high voltage. When pole A of switch SW1 is turned on, high voltage is removed from terminal 1 and capacitor 180 slowly discharges through resistor 182, slowly increasing the resistance through transistor 178. Pole B of switch SW1 now also connects the reference potentiometer to resistor 132, and the reference voltage slowly increases to its nominal value when transistor 178 is shut off.

Due to loading by transistor 178 when switch SW1 is in the off position, it is necessary to connect the wiper arm of potentiometer 124 through pole B of switch SW1 to another divider 184, which feeds the correct reference voltage $V_{SET}$ to indicator 120 through selector switch SW3.

The control system shown in FIG. 3 can be operated in the pressure or vacuum (negative gauge pressure) mode as well as the flow rate control mode with minor changes. In this case the reference potentiometer 124 will be set to provide the desired value of vacuum reference voltage, $V_{VR}$, and the measured output of the vacuum sensor, $V_{VS}$, will be applied to input resistor 138. A scaling circuit (not shown) will be used so that the range of voltage $V_{VS}$ will correspond to that of $V_{VR}$. Set point potentiometer 186 of voltage divider 184 will be adjusted to provide an appropriately scaled vacuum quantity on display 120. Where both flow rate control and vacuum control will be used intermittently, it would be advantageous to use separate flow rate and vacuum reference and set point potentiometers. Voltages $V_{FR}$ or $V_{VR}$, $V_{FS}$ or $V_{VS}$ and $V_{SET}$ for either flow rate or vacuum would be connected to the system through a multipole selector switch.

Correction of the differential pressure that is measured across the taps to provide an output that is proportional to actual volume flow rate referred to ambient atmospheric conditions is explained below.

$$\Delta P_1 = K_v Q_1 = K_v Q_0(P_0/P_1) = K_v Q_0(P_0/P_1)$$

$$Q_0 = K_p \Delta P_1(P_1/P_0)$$

$$P_1/P_0 = P_0 - P_{VAC}/P_0 = 1 - (P_{VAC}/P_0)$$

$$Q_0 = K_p \Delta P_1(1 - P_{VAC}/P_0)$$

Q is volume flow rate, $\Delta P$ is pressure drop cross the laminar flow sensor taps, P is air pressure, $\rho$ is air density, $K_v$ and $K_p$ are constants, subscript 1 refers to condition at laminar flow sensor, subscript 0 refers to condition at standard atmosphere, subscript VAC refers to a vacuum, or negative pressure referred to standard atmospheric pressure.

It is obvious that electrical voltages can be substituted as analogs of the pressures indicated above.

Figure 4:
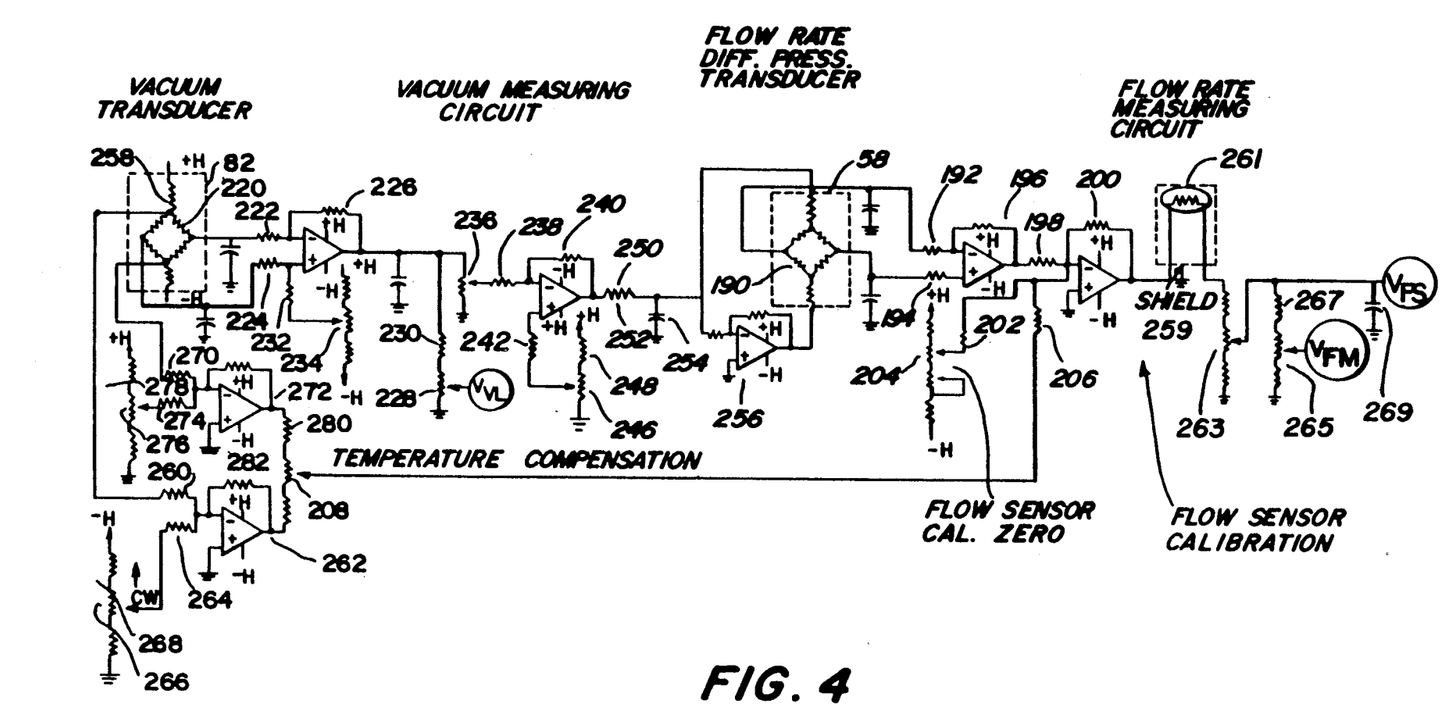
FIG. 4 is an electrical schematic diagram of a pressure and flow measuring circuit.

A flow rate and pressure measuring circuit is shown in FIG. 4, that can be used in the system shown schematically in FIG. 2 and together with the control circuit of FIG. 3. This consists, essentially, of two coupled independent circuits, one for the measurement of flow rate with a differential pressure type of laminar flow sensor, and the other for the measurement of pressure, in this case negative gauge pressure or vacuum. Considering first the flow rate measuring circuit, the differential pressure across the laminar flow element is sensed by differential pressure transducer 58 of the strain gage bridge type. The strain gage bridge 190 is excited by positive and negative voltages that are highly regulated at approximately the same magnitude, so that at zero differential pressure (zero flow rate), the bridge output voltages at the centers of the two branches are near ground. The outputs of the strain gage bridge 190 of transducer 58 are fed into input resistors 192 and 194 of differential amplifier 196, the output of which is a voltage proportional to the differential pressure, and, therefore, the volumetric flow rate, and which, in turn, is supplied to one input resistor 198 of a summing amplifier 200. A zeroing voltage is also supplied to summing amplifier 200 through input resistor 202 from the wiper arm of balancing potentiometer 204, which is part of a voltage divider between two high regulated voltages of opposite polarities. Potentiometer 204 can be adjusted in either direction to eliminate small voltages of either polarity that might appear at the output of amplifier 200 at zero flow rate. A third voltage is applied to the summing point of amplifier 200 through input resistor 206 from a temperature compensation network 208, so as to correct for changes in the output of amplifier 200 due to temperature variations. The output of amplifier 200, then, is a corrected voltage proportional to the volumetric flow rate through the laminar flow element.

Referring now to the vacuum measuring circuit, the negative gauge pressure at the inlet, or upstream tap of the laminar flow element, is sensed by a gauge pressure transducer 82 of the strain gage bridge type. Strain gage bridge 220 is excited by positive and negative voltages that are highly regulated at approximately the same magnitude so that at zero atmospheric pressure (zero vacuum), the bridge output voltages at the center of the two branches are near ground. The outputs of the strain gage bridge 220 are fed into input resistors 222 and 224 of differential amplifier 226, the output of which is a voltage proportional to the vacuum. The voltage $V_{VL}$ of the proper scale, shown on indicator 120, is provided from the wiper arm of potentiometer 228 of voltage divider 230. A zeroing voltage is applied to amplifier 226 through input resistor 232 from the wiper arm of balancing potentiometer 234, which is part of a voltage divider between two high regulated voltages of opposite polarities. Potentiometer 234 can be adjusted in either direction to eliminate small voltages of either polarity that might appear at the outlet of amplifier 226 at zero vacuum. A portion of the output voltage of amplifier 226, which is proportional to the measured vacuum, is applied through potentiometer 236 to input resistor 238, which is connected to the negative input terminal of differential amplifier 240. The positive terminal of amplifier 240 is connected through input resistor 242 to the wiper arm of potentiometer 246 of voltage divider 248 between ground and a high regulated voltage. The output voltage of amplifier 240 then is a voltage which is proportional to a constant minus a second term, which second term is proportional to a second constant multiplied by the vacuum. As previously explained, this voltage is equivalent to a term related to the actual vacuum, by which the differential pressure across the taps of the laminar flow element must be multiplied to compensate for increased velocity due to lower density at the negative pressure, so as to provide an output related to the true volumetric flow rate referred to ambient atmospheric conditions. The output of amplifier 240 passes through an electronic filter 250 consisting of a series resistor 252 and shunting capacitor 254 to minimize ripple in the flow rate correcting voltage that might be due to flow and, therefore, pressure pulsations. The filtered correcting voltage is applied to the positive excitation terminal at one end of the strain gage bridge 190 of differential pressure transducer 58. The filtered correcting voltage is also applied to the input of inverting amplifier 256, whose output is a voltage of the same magnitude but opposite polarity as that applied to the positive excitation terminal, and which is applied to the negative excitation terminal of strain gage bridge 190 of the differential pressure transducer 58. As explained previously, this achieves a multiplication in the flow rate differential pressure transducer to provide a corrected flow rate related output.

Pressure transducers 58 and 82 utilize semiconductor strain gages which are temperature sensitive. These transducers are temperature compensated through thermistor networks placed between the inlet and outlet of the transducer and the positive and negative excitation terminals of the strain gage bridge. Although these thermistor networks eliminate most of the deviations caused by varying temperatures, there is still a residual temperature error, mostly in a zero shift such that a positive or negative voltage will appear at the transducer outputs, when the applied pressures are zero, but also, to a lesser degree, in a change in span with temperature. The transducers being used are Sensym Type SCX C Series transducers in which, when the transducer is excited by a constant regulated voltage, temperature compensating voltages varying in opposite sense are available at opposite ends of the bridge network, due to the action of the temperature compensating thermistors. The variation of these temperature sensitive voltages is linear over the temperature range of interest and these are used in the temperature compensating network 208 to apply temperature compensating voltages to flow rate output amplifier 200 through resistor 206. Since zero shift of these types of transducers can occur randomly in either a positive or negative sense, even among transducers of the same type and range, it is necessary that the temperature compensating network be able to supply a correcting voltage of either polarity. The temperature sensitive voltages have a variation that is small compared to their average values, and, therefore, it is necessary to balance out the constant portion of the voltage. The positive varying temperature sensitive voltage is obtained from junction 258, and it is applied to input resistor 260 of summing amplifier 262. A constant negative voltage is applied to the input resistor 264 of amplifier 262 from the wiper arm of potentiometer 266 in negative voltage divider 268. Similarly, the negative going temperature voltage is applied to input resistor 270 of summing amplifier 272, and a constant positive voltage is fed to summing amplifier 272 through input resistor 274 from the wiper arm of potentiometer 276 in positive voltage divider 278. The output voltage of amplifier 272 is a small positive going voltage, and the output voltage of amplifer 262 is a small negative going voltage. The two outputs are connected by voltage divider 280, and the temperature compensating voltage which is fed to amplifier 200 is obtained from a central potentiometer 282 whose wiper arm can be moved in either direction to provide positive or negative temperature compensating voltages. In practice, the zero shift with temperature of the flow rate differential pressure transducer is determined by a temperature test, and an appropriate positive or negative voltage from potentiometer 282 is applied to the input of amplifier 200 to minimize the change. The temperature shifts of the pressure transducers are usually very small when related to full scale. Since it is desired to keep the pressure drop across the laminar flow element to a small value, only a portion of the flow range of the differential pressure transducer is utilized, and, therefore, small zero shifts such as those that are caused by temperature, have a much greater significance than is ordinarily the case. The vacuum transducer is operated at full scale so that the zero shifts are insignificant, and no temperature correction is required.

To obtain a voltage which is proportional to the true volumetric flow rate referred to ambient conditions, it is also necessary to correct the measurement for the temperature of the air at the inlet of the laminar flow element. Although this is a minor effect compared to that of the vacuum, it is, nonetheless, required for temperature changes in excess of approximately plus or minus 5% of the absolute calibration temperature. To provide this temperature correction, the output voltage of amplifier 200 is fed to a voltage divider which includes the linear temperature sensitive resistor element 261. A voltage proportional to the true volumetric flow rate is fed from the wiper arm of calibration potentiometer 263 of voltage divider 259. A portion of this voltage at the proper scale to be displayed on indicator 120, is obtained from the wiper arm of potentiometer 265 of voltage divider 267. The output voltage $V_{FS}$ is further filtered by capacitor 269 and a portion of voltage divider 258.

To calibrate the system, the vacuum output is zeroed through potentiometer 234, and then the flow rate output is zeroed through adjustment of potentiometer 204. Following this, a known flow rate is drawn through the system at zero vacuum and measured by a standard flowmeter of higher accuracy than that of the system of FIG. 4. The flow sensor calibration potentiometer 263 is adjusted until the output voltage corresponds with the flow rate indicated by the standard meter. Following this, a restriction is placed on the inlet to the sampler to create a vacuum, and vacuum compensating potentiometer 246 is adjusted to provide the required correction so that the output is equivalent to a measurement by the standard meter, which is connected in the inlet at ambient conditions.

Figure 5:
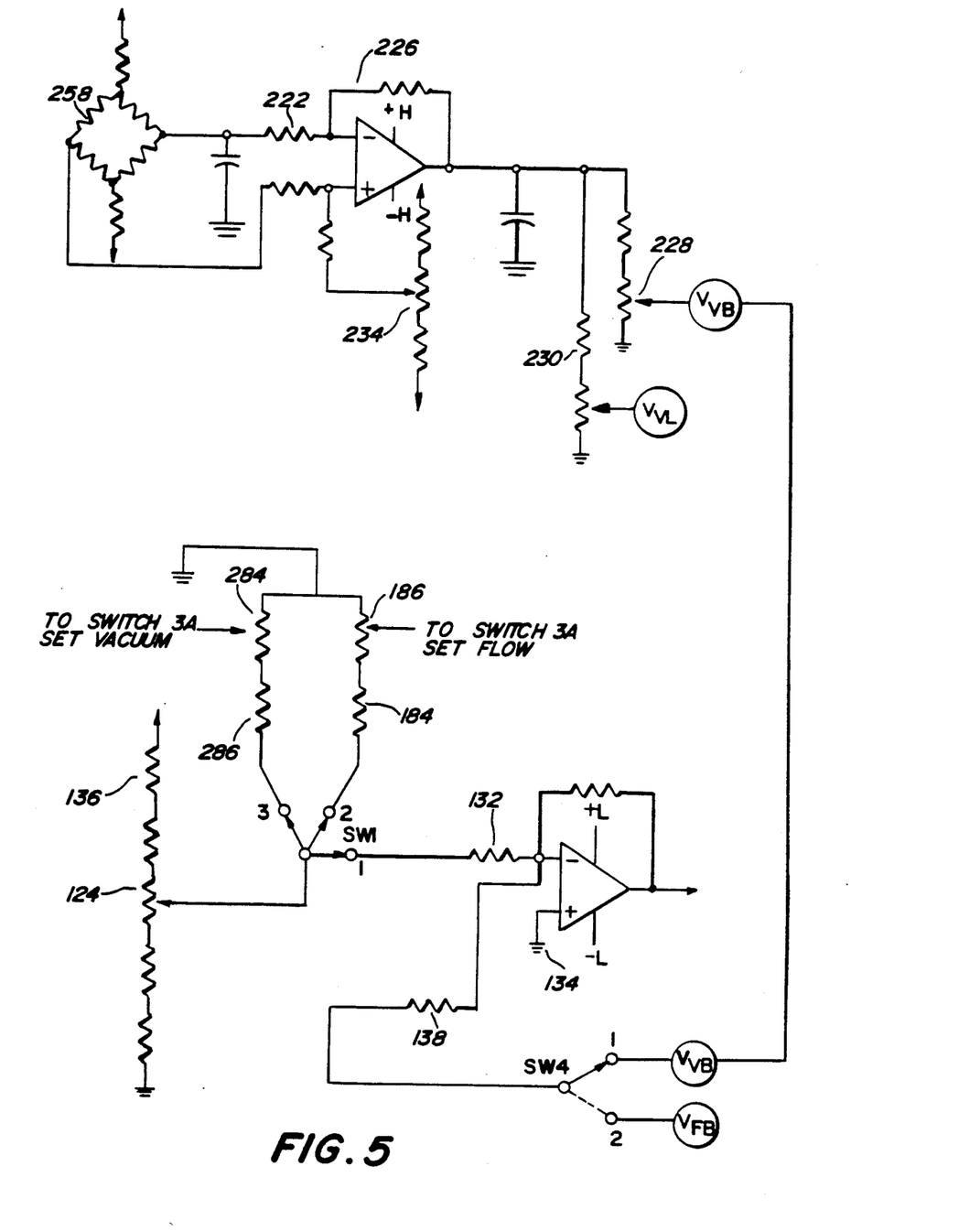
FIG. 5 is a partial schematic diagram showing application of the system to pressure control.

FIG. 5 illustrates the combined optional vacuum and flow rate control which is briefly described in the discussion for FIG. 3. Both the vacuum and flow rate reference voltages are obtained from the wiper arm of potentiometer 124 in voltage divider 136. The reference voltage is fed to the common terminal of switch SW1, which is now shown as a three-position switch. In position 1 of switch SW1, the reference voltage is fed directly to input resistor 132 of amplifier 134. In position 2 the reference voltage is connected to a voltage divider 184, where the flow rate setting is obtained from the wiper arm of potentiometer 186. In position 3 of switch 1 the reference voltage is fed to potentiometer 284 in voltage divider 286, from which the vacuum set voltage is fed from the wiper arm to switch 3A. The measured vacuum feedback voltage $V_{VB}$ is fed from potentiometer 228 to terminal 1 of switch 4, and the flow rate feedback voltage $V_{FB}$ is fed to terminal 2 of switch 4. In the flow rate control mode, switch 4 is set to position 2, and the flow rate feedback voltage is fed to input resistor 138 of amplifier 134. When the power is off, switch SW1 is set to position 2 so that the flow rate can be set on indicator 120 at the desired quantity. Similarly, in the vacuum control mode, switch 4 is set to position 1, and switch 1 is set to position 3 for the same reason.

Figure 6:
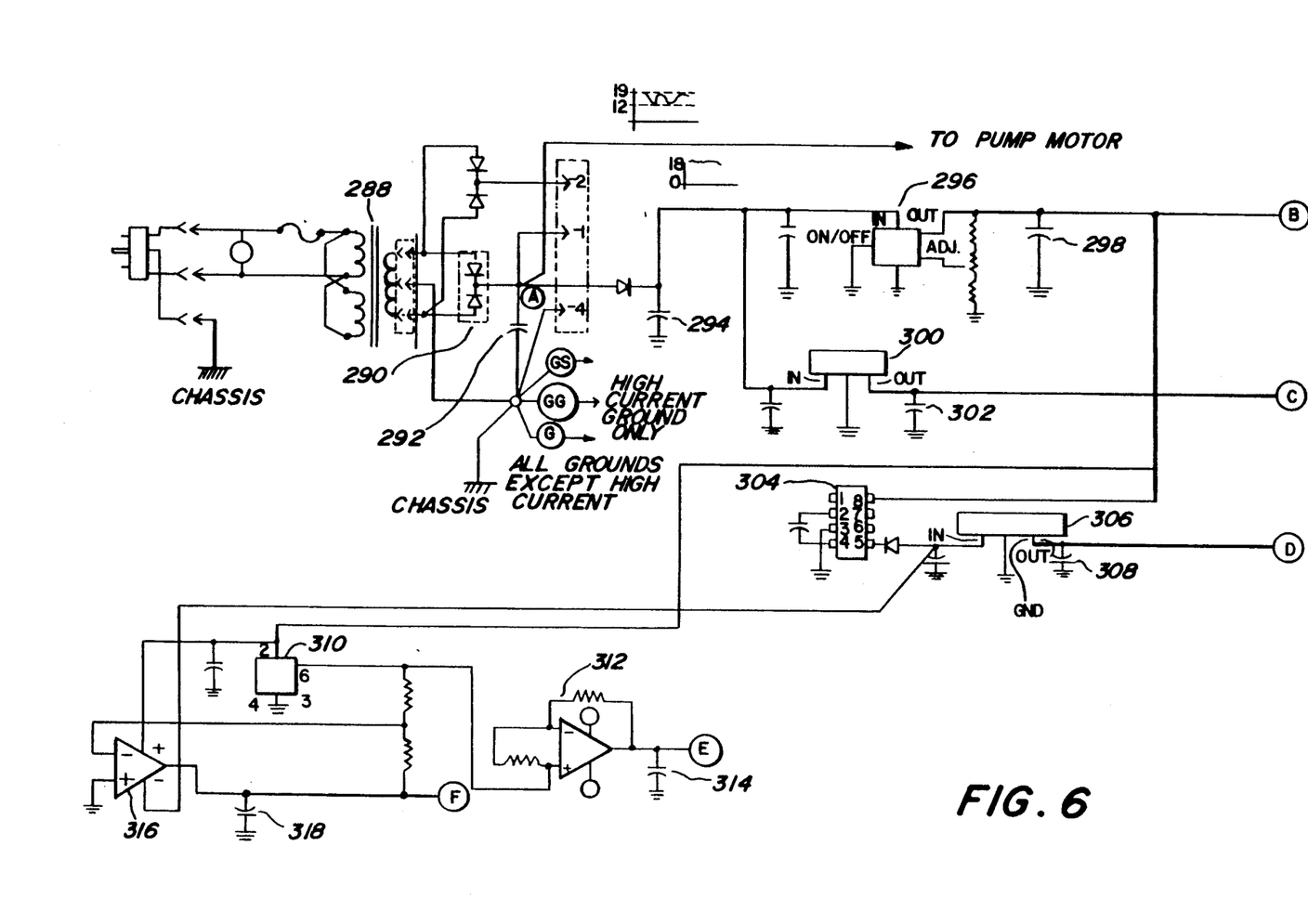
FIG. 6 is an electrical schematic diagram of the power supply system.

An electrical schematic diagram of power supply 118 is shown in FIG. 6. For AC operation, power is supplied to the primary stepdown transformer 288. The output of the secondary is fed to full wave rectifier 290 which provides pulsating DC at point A. Since the bulk of the current is used to drive the pump motor, only a limited amount of filtering is supplied by capacitor 292 in order to keep the size of the capacitor and, therefore, the power supply of a portable unit small. The pulsating DC that is used to drive the pump motor, typically, will have a ripple of between 12 and 19 volts. DC for the control is subject to additional filtering through capacitor 294, and it is passed to a voltage regulator 296, which is used to supply a high voltage with moderate regulation for further refinement to positive and negative voltage levels used to drive operational amplifiers, excite the transducers, and be used as reference voltages. The voltage output of regulator 296 is led to terminal B, and high voltage, typically of 13 volts DC, is further filtered by capacitor 298 to provide a low ripple supply. The voltage to the input of regulator 296 is also fed to regulator 300 whose output, which is connected to terminal C, is at a low positive voltage, typically of +5 volts, for powering operational amplifiers. Output capacitor 302 provides additional filtering to reduce the ripple to an acceptable level. The high voltage is also fed to a DC inverter 304, which through regulator 306 supplies a negative voltage to terminal D at a low level which is the same level, but of opposite polarity, to that of terminal C. typically of −5 volts. A high degree of filtering is provided by capacitor 308. The high voltage from terminal B is also provided to precision regulator 310, which supplies a highly regulated voltage at a high positive level, typically +10 volts DC. This voltage is amplified in the unity gain amplifier 312 to terminal E to avoid loading of the precision regulator, and a high degree of filtering is supplied by capacitor 314. The output voltage of precision regulator 310 is fed to an inverting amplifier 316, which supplies a negative voltage at the same amplitude, but of opposite polarity, as the high positive voltage supplied by regulator 310 and amplifier 312 at terminal E, and supplies a high level negative voltage at terminal F, with a high degree of filtering being supplied by capacitor 318. The positive high voltage for inverting capacitor 316 is obtained from the high (13 volt) positive supply from terminal B. The negative high voltage supply to amplifier 316 is obtained from the output of DC inverter 304 as a negative voltage, typically 12 volts, so that both precision regulator 310 and inverting amplifier 316 can supply highly stable, precisely regulated high positive and negative voltages. The positive and negative low DC voltages available at terminals C and D are used to energize amplifiers and electronic components where the precision regulator is not required, and where the high voltage is not necessary. By this means, current drain from the power supply is reduced and the size of the precision regulators is minimized.

Figure 7:
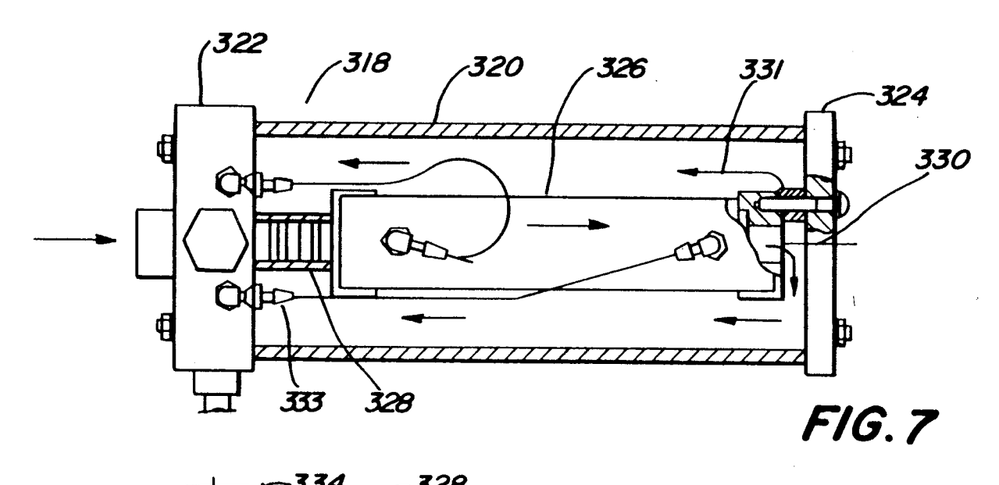
FIG. 7 is plan view in partial section of a combined pulsation damper and linear flow sensor.
Figure 8:
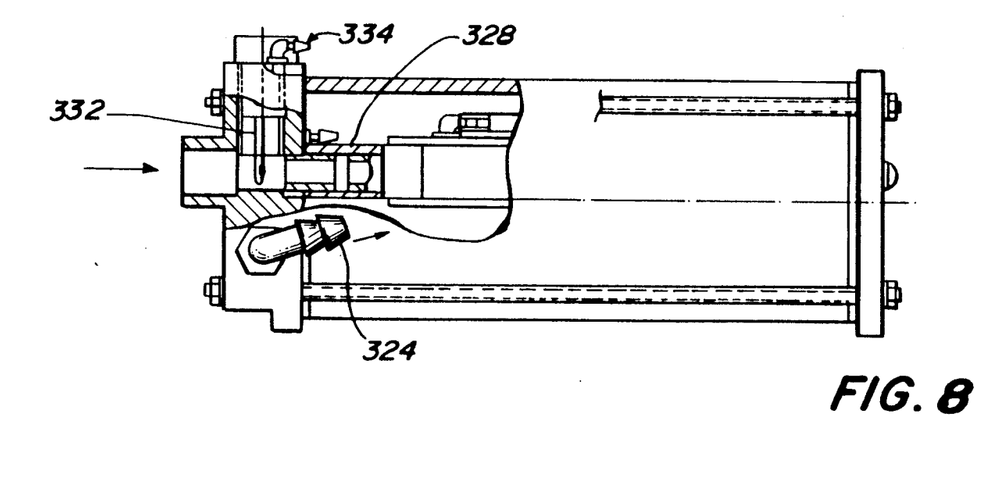
FIG. 8 is a side view in partial section of the pulsation damper and linear flow sensor assembly shown in FIG. 7.

A preferred means of assembling the laminar flow sensing element with the pulsation damper in the system of FIG. 2, is illustrated in FIGS. 7 and 8. The principal reason for this arrangement is to reduce temperature gradients in the laminar flow sensing element which could cause errors on the order of plus or minus 5% each due to the changes in air viscosity and density, with temperature fluctuations throughout the normal temperature range. Another temperature problem is the fact that, within a portable case, heating of the internal atmosphere due to waste energy from the pump motor and, to a lesser extent, from power of electronic components, can provide a substantial temperature increase. As shown in FIGS. 7 and 8, the pulsation dampening chamber 318 consists of a cylindrical housing 320 held between an inlet block 322 and a flat end piece 324. A flow sensor 326 is retained axially between the front block and the end piece. Air enters block 322 from the left and passes through a connection 328 into the flow sensor. The air flows axially through the sensor and out through port 330 into chamber 331 in housing 320. The air enters a manifold in block 322 and then is drawn out through fitting 324 into the pump inlet. Inlet temperature sensor 98 shown schematically in FIG. 2 and FIG. 4 is now located within a temperature probe 332, which is located directly in the air stream entering the flow sensor. Upstream and downstream pressure taps of the laminar flow differential pressure flow sensor are connected to internal fittings 333 in block 322 and then through lines on external fittings 334 to the pressure transducers.

Flow sensor element 326 is surrounded by the same air that is pumped through it, and which insulates the flow sensor and keeps its temperature very close to that of the incoming air. Housing 320 can be made of some plastic material with a reasonably low thermal conductivity, further insulating the flow sensor from the environment.

Figure 9:
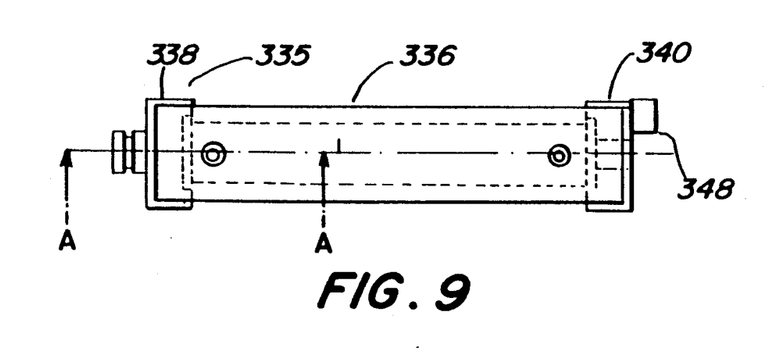
FIG. 9 is a plan view of one type of linear flow sensor assembly.
Figure 10:
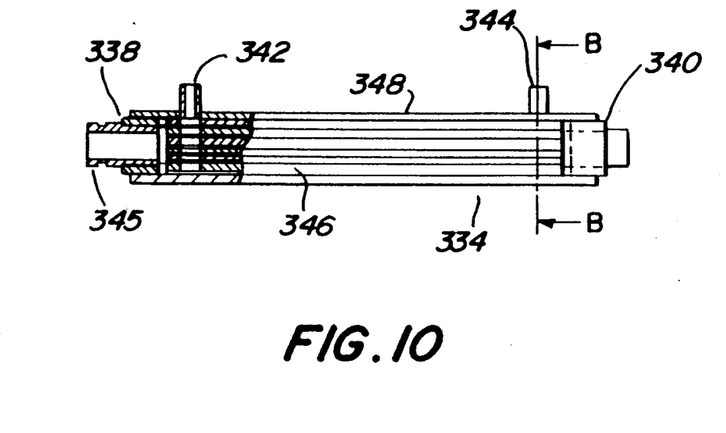
FIG. 10 is a sectional view along line AA of the linear flow sensor assembly shown FIG. 9.
Figure 11:
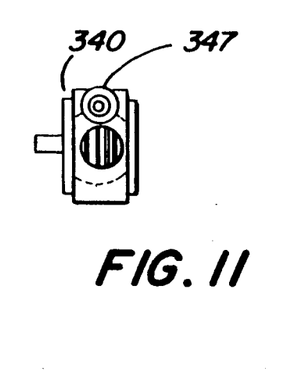
FIG. 11 is an end view of the linear flow sensor assembly shown in FIG. 9.
Figure 12:
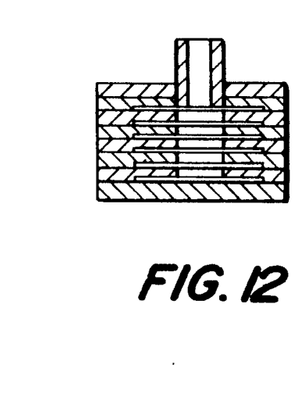
FIG. 12 is a sectional view along line BB of the linear flow sensor assembly shown FIG. 9.
Figure 13:
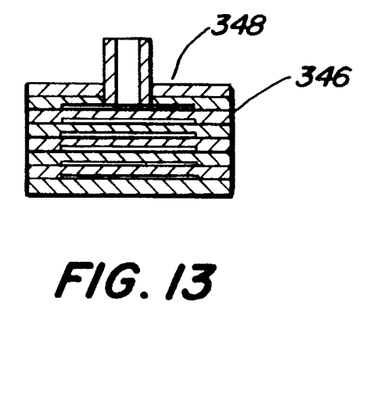
FIG. 13 is a sectional view of a linear flow sensor assembly similar to that shown FIG. 12, with an alternate pressure tap arrangement.
Figure 14:
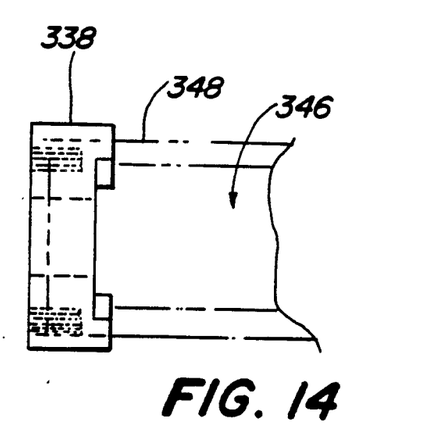
FIG. 14 is a plan view of the end block of the linear flow sensor assembly shown in FIG. 9 that retains the stack of linear flow elements.
Figure 15:
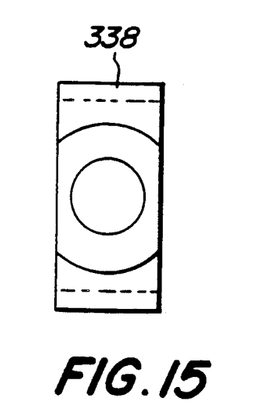
FIG. 15 is an end view of the end block shown in FIG. 14.
Figure 16:
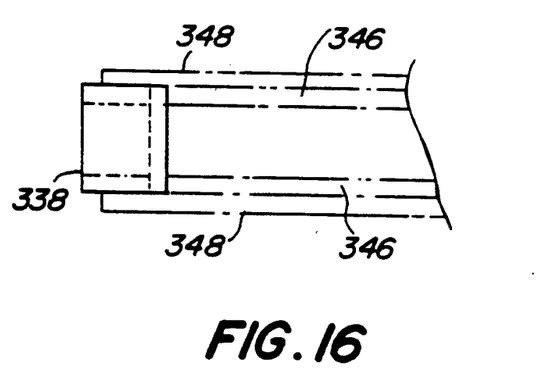
FIG. 16 is a side view of the end block shown in FIG. 14.

The preferred construction of a laminar flow element for a linear differential pressure flow sensor is illustrated in FIGS. 9 through 16. FIGS. 9, 10 and 11 show the overall configuration of the laminar flow element assembly 335. The assembly consists of a stack 336 of individual flow channels 346 held between inlet and outlet end blocks 338 and 340. Spaced apart inlet pressure tap 342 and outlet pressure tap 344 transmit upstream and downstream pressures through external tubes to the pressure and differential pressure transducers. The inlet tap must be no closer than a minimum distance to the inlet edge of the flow stack, which is defined as a sufficient distance away from the inlet edge of the flow channel so that a fully developed laminar flow pattern is present. The inlet block 338 has a fitting 345 for connection to the manifold in the front inlet block 322 of the pulsation dampener. A fitting is not required in inlet block 340 since the flow from the laminar flow element discharges directly into the interior of housing 320. Spacers 347 (one not shown) are provided to maintain adequate clearance between the end block 340 and the end plate 324 of the pulsation dampener so as to insure unobstructed flow from the flow element to the chamber 332 in the interior of housing 320. FIGS. 12 and 13 are sections along line BB showing the arrangement of the flow channels and alternate pressure taps. The flow channels 346 of stack 336 consist of one or more rectangular paths with a very large cross sectional aspect ratio of width to height. The height and width of a rectangular flow path are determined from practical geometrical considerations. The height must not be so small that it cannot be reproduced by an economical procedure (e.g. machining, molding) or that manufacturing tolerances could cause a large variation in the flow resistance. With a limiting tolerance for economical production taken on the order of 0.001", the height of the flow path should be not much less than 0.010". A range of 0.008" to 0.016" is reasonable for the flow rates under consideration for air sampling. The width is also limited by considerations of uniformity, thickness and flatness. In order to provide reasonable rigidity and absence of deflections, the thickness of each channel has been taken as between 0.060" and 0.125". From this consideration, the favorable width of the flow path would be between $\frac{3}{8}$ and $\frac{3}{4}$ of an inch. Based on these considerations for the cross section of the flow path, the area that is required is that which, for the range of volumetric flow rates to be accomodated, provides flow rates in the laminar region, having a Reynolds number not greater than 1,000, and preferably not greater than 500. For the maximum flow rate to be measured, and the maximum allowable Reynolds number for which every point of the channel will experience laminar flow, the total cross sectional area is determined, and for the unit channel area determined by the height and width of an individual flow path, the number of parallel channels is determined.

As shown in FIGS. 10 and 12, a pressure tap is placed through a top plate 348 (inactive) into the flow region of the top channel. An aperture is made in the flow channel along the axis of the tap for pressure equalization among the channels. It should also be possible to have a flow tap with only a single channel, with the parallel channels considered to be bypasses, which will maintain laminar flow by reducing the velocity to the required range. Such bypass type flowmeters are widely used particularly with orifices and rotameters. The alternate construction shown in FIG. 13 has the advantage of being simpler and more economical, but at the risk of a greater variation of flow characteristics.

The flow channel stack 336 is shown in FIGS. 9 through 13 as six parallel 346 channels that are retained between outer inactive plates 348, which extend longitudinally beyond the inlet and outlet of the stack so as to overlap the top and bottom of end blocks 338 and 340. The ends of flow channels 346 butt up against the side walls of the end blocks to provide a seal and prevent leakage. A counterbore in the interior of each end block provides a volume for direction of air between the flow paths in the channels and the outlet port of the end blocks. This assembly arrangement is more clearly evident by referring to FIGS. 14, 15 and 16.

Rectangular flow paths for the maintenance of laminar flow in the differential pressure flow sensing element have previously been described, but no reference has been made for the type of construction shown in FIGS. 9 through 16, particularly for multiple channels in a parallel stack arrangement, which will be needed for the maintenance of laminar flow at most flow rates except for very low flow rates, where a single channel might be sufficient. The limitation on the use of multiple channels would be in the height of the flow path that is required because if this is significantly less than the order of magnitude stated above, then it would be very difficult and uneconomical to produce them with the required precision.

Another feature of the stacked parallel rectangular flow channels, which are used in laminar flow sensing element 336, is the material and means of joining the channels into an integral unit without danger of leakage or excessive difference in the flow characteristics. Although, conceptually, any material could be used, there is a problem in the use of hard materials such as metals. To provide a good seal surface in the metal-to-metal contact between the channels, extreme flatness and fine surface finish are required, which can greatly increase the cost of the flow sensing element. As an example, it is only necessary to consider the prices of machinists' gage blocks. If such flatness and fine surface finish are not maintained, then there will be considerable leakage in the surface between the flow channels. This could be conventionally overcome by the use of resilient gaskets or similar resilient bonding coating between the surfaces. In the case of gaskets, to obtain a good seal, some deformation is required, and the resilience and possible set of the gasket could be of the same order of magnitude as the height of the flow path, which could be less than ten-thousandths of an inch. The same problem occurs with the use of a resilient adhesive which would serve as a bond and also a gasket. With an adhesive such as epoxy cement, which dries to a solid surface, there is a problem of maintaining uniform coating thickness, and the danger of having substantial variations in the height of the flow path, making it very difficult to achieve flow sensing elements with reproduceable characteristics. The initial construction of elements shown in FIGS. 9 through 16 utilized aluminum as a material, and sealing between the surfaces was attempted with thin rubber gaskets, as well as resilient and hard setting bonding materials. Considerable difficulty was experienced in achieving seals and uniform characteristics.

It was finally determined that an optimum material for this construction needed to be one of sufficient rigidity to maintain the channel dimensions under the moderate stresses experienced, and with sufficient elasticity so that under moderate pressures, the surfaces would provide sufficient cold flow for satisfactory sealing. However, means of fastening the parallel elements present a problem, as clamping could result in permanent set that could cause leaks. It was found that a solvent-weldable plastic, such as acrylic, is a uniquely satisfactory material for this application. Although many plastics, for example, polystyrene, are softened by some solvents, this can be a rather lengthy procedure. Acrylic plastics can be joined together with the use of a dichloromethane solvent solvent, also known commercially as Res-N-Bond, in which the solvent welding occurs relatively quickly and provides the strength almost equivalent to that of the parent material. In practice it was found that by making the flow channels of acrylic plastic, clamping them together for the bonding operation, and then applying the Res-N-Bond solvent externally into the interfaces between the elements, the solvent could be drawn in between the flow channels by capillary action, forming a tight and uniform seal. Similar sealing is made to the end blocks 338 and 340 which are also made of acrylic plastic. The flow paths and the channels are preferably machined, in order to obtain the best dimensional control, although they could conceivably be molded, if adequate tolerances on the order of 0.001" can be maintained. The use of solvent-weldable acrylic can be used to make available very effective differential pressure laminar flow elements at comparatively low cost.

I claim:

1. A controlled sampler to draw a sample of air or other gas through a contaminant collection device in a manner to maintain a flow-related parameter at a selected constant value, comprising:

an inlet to the sampler, a DC motor-driven pump having an inlet connected to the sampler inlet through a line to pump air or gas through the sample inlet, a reference element with an output, to provide a reference signal that is linearly related to the selected value of the parameter being maintained, a feedback element with an output, sensitive to the parameter being maintained, and connected between the sampler inlet and the pump inlet so as to provide a feedback signal that is linearly related to the actual value of the parameter, differential means to compare said reference signal with said feedback signal to provide an output signal that is linearly related to the error between the selected and measured values of the parameter being maintained, an integrator with an input connected to the output of the differential means, to provide an output signal related to the integral of the error signal to the input of a summer, means between the differential means and the summer to provide a signal to the summer proportional to the error signal, said summer providing a signal constituting the sum of said integral and proportional signals to a driver, which modulates electric power to said DC motor, so as to change the speed of the motor-driven pump and the flow rate through the pump in a direction to reduce the error signal to a null.

2. A controlled sampler as defined in claim 1, wherein the sample is air.

3. A controlled sampler to draw a sample of a gas through a contaminant collection device in a manner to maintain a flow related parameter at a selected constant value, comprising:

an inlet to the sampler, an electric motor-driven pump having an inlet connected to the sampler inlet through a line to pump said gas through the sampler inlet, a reference element with an output, to provide a reference signal that is linearly related to the selected value of the parameter being maintained, a feedback element with an output, sensitive to the parameter being maintained, and connected between the sampler inlet and the pump inlet so as to provide a feedback signal that is linearly related to the actual value of the parameter, differential means to compare said reference signal with said feedback signal to provide an output signal that is linearly related to the error between the selected and measured values of the parameter being maintained, an integrator with an input connected to the output of the differential means, to provide an output signal related to the integral of the error signal to the input of a summer, means between the differential means and the summer to provide a signal to the summer proportional to the error signal, said summer providing a signal constituting the sum of said integral and proportional signals to a driver, which modulates electric power to said motor, so as to change the speed of the motor-driven pump and the flow rate through the pump in a direction to reduce the error signal to a null.

4. A controlled sampler as defined in claim 3, in which the flow-related parameter is a volumetric flow rate of said sample of air or gas, and the feedback element includes a flow sensor with an output that is linearly related to said volumetric flow rate.

5. A controlled sampler as defined in claim 4, in which the flow sensor is a laminar flow element, and the output of the flow sensor is a differential pressure across said element.

6. A controlled sampler as defined in claim 5, in which the flow sensor includes spaced apart pressure taps in the direction of flow and including a differential pressure transducer with ports connected to the pressure taps, said differential pressure transducer having an output.

7. A controlled sampler as defined in claim 6, in which the feedback element includes a pressure transducer having an output, connected to the line between the sampler inlet and the flow sensitive element, to correct the feedback signal and pressure changes at the sampler inlet, and to provide a feedback signal related to the actual volumetric flow rate.

8. A controlled sampler as defined in claim 7, in which the differential pressure transducer includes a strain gage bridge with an output and the pressure transducer includes a strain gage bridge with an output, and in which the differential pressure strain gage bridge is excited by a fixed voltage and the differential pressure strain gage bridge is excited by a voltage related to the output of the pressure bridge, the output of the differential pressure strain gage bridge being used to provide a corrected feedback signal.

9. A controlled sampler as defined in claim 6, in which the feedback element includes a temperature sensor having an output, connected to the line between the sampler inlet and the flow sensitive element to correct the feedback signal for temperature changes at the sampler inlet.

10. A controlled sampler as defined in claim 6, including a pneumatic filter between a pressure tap in the flow sensor and a port in the differential pressure transducer to attenuate pulsations, said pneumatic filter includes a restrictor.

11. A controlled sampler as defined in claim 7, in which the actual volumetric flow rate is that at ambient atmospheric conditions.

12. A controlled sampler as defined in claim 4, including means to integrate the volumetric flow rate output with time to provide an output related to the total volume passing through the flow sensor.

13. A controlled sampler as defined in claim 4, in which the gas is ambient air, including a bypass valve connected to the line immediately before the pump inlet, to feed air directly from the atmosphere into the pump inlet, in parallel with air flowing through the flow sensor, so that at relatively low flow rates through the sensor, the pump will be operating at optimal speeds with acceptably high pulsation frequencies.

14. A controlled sampler as defined in claim 4, in which the feedback element includes a pressure sensor with an output to correct the output of the flow sensor for changes in pressure.

15. A controlled sampler as defined in claim 3, in which the flow-related parameter is the negative or positive inlet pressure and the feedback element is a pressure transducer with an output that is linearly related to the pressure at the sampler inlet.

16. A controlled sampler as defined in claim 15, in which said pressure transducer is connected through a pneumatic filter, which includes a restrictor.

17. A controlled sampler as defined in claim 3, in which a driver of the pulse-width modulating type modulates electric power to said motor.

18. A controlled sampler as defined in claim 3, including starting means to supply a slowly increasing reference to the differential reference and feedback comparing means, to prevent saturation of the control system and high pump speeds when the system is started, due to the very large initial differential.

19. A controlled sampler as defined in claim 3, including a pulsation damper connected between the sampler inlet and the pump inlet.

20. A controlled sampler as defined in claim 19, in which said feedback element includes a laminar flow sensing element, with an inlet and an outlet, said pulsation damper includes a housing with an outlet connected to the inlet of said motor-driven pump, said laminar flow sensing element is contained within said housing, the inlet of the laminar flow element is connected to the sampler inlet and the outlet of the flow sensing element discharges into the interior of said housing.

21. A controlled sampler as defined in claim 3, wherein the sample is air.

22. A controlled sampler as defined in claim 11, in which said feedback element includes compensating means to minimize the zero shift with temperature of the output of said feedback element.

* * * * *